United States Patent
Dever et al.

(10) Patent No.: US 9,489,809 B1
(45) Date of Patent: Nov. 8, 2016

(54) WEARABLE INDICATOR DEVICES AND METHODS OF USING SAME

(71) Applicant: Heads Up Display Inc., Buffalo, NY (US)

(72) Inventors: Brendon Charles Dever, Buffalo, NY (US); William Clark Dever, Kenmore, NY (US); Brian Raymond Bezanson, Buffalo, NY (US); Robert Maefs, Buffalo, NY (US); George Hampton, Buffalo, NY (US)

(73) Assignee: Heads Up Display Inc., Buffalo, NY (US)

( * ) Notice: Subject to any disclaimer, the term of this patent is extended or adjusted under 35 U.S.C. 154(b) by 0 days.

(21) Appl. No.: 14/749,630

(22) Filed: Jun. 24, 2015

Related U.S. Application Data

(60) Provisional application No. 62/016,631, filed on Jun. 24, 2014.

(51) Int. Cl.
 *G08B 5/36* (2006.01)
(52) U.S. Cl.
 CPC ........................... *G08B 5/36* (2013.01)

(58) Field of Classification Search
 CPC ........................................................ G08B 5/36
 See application file for complete search history.

(56) References Cited

U.S. PATENT DOCUMENTS 8,183,997 B1 * 5/2012 Wong ................... G01S 3/8036
340/4.4

\* cited by examiner

*Primary Examiner* — Leon Flores
(74) *Attorney, Agent, or Firm* — Hodgson Russ LLP

(57) ABSTRACT

Disclosed are wearable indicator devices and methods of using same. The device is a head-mounted device for detecting an alert condition and providing an alert to a user. The device has a display unit with one or more LEDs and a driver circuit configured to control the brightness of the one or more LEDs. The device also has a control unit having a microprocessor, a memory buffer in electronic communication with the microprocessor, a microphone in electronic communication with the microprocessor, and a radio transceiver configured to interface with an external computing system. The microprocessor can be configured to gather audio samples from the microphone, analyze one or more gathered audio samples for an alert condition, transmit the alert condition, and control the LEDs based on the alert condition.

9 Claims, 14 Drawing Sheets

WEARABLE INDICATOR DEVICES AND METHODS OF USING SAME

CROSS-REFERENCE TO RELATED APPLICATIONS

This application claims priority to U.S. Provisional Application No. 62/016,631, filed on Jun. 24, 2014, the disclosure of which is incorporated herein by reference.

FIELD OF THE DISCLOSURE

The invention relates to a wearable indicator devices and methods of using same.

BACKGROUND OF THE DISCLOSURE

Accidents in the workplace can be catastrophic and expensive. In working environments such as construction, transportation, defense, logistics industries, users need to be able to keep their line of focus while being prompted of the hazards around them. Previously, the industry used safety alarms for this purpose.

Safety alarms are often fixed-positioned devices. As a result, these alarms are limited in the types of communication they can transmit. Hazards often go unnoticed because of the limited ability to transmit warnings to users individually or en mass. This presents a problem for users, their employers, and their insurance companies.

Current wearable solutions involve augmented reality products that overlay data on as much of the wearer's view as possible. These solutions utilize on-board computation, high resolution displays, and generally have broadcasting capabilities. Each wearable device is complex and expensive. Current solutions require precision alignment and larger, heavier, batteries.

A user needs a simple indication of data that is pertinent to their lives while maintaining their line of sight. This data to be recorded and analyzed on an individual basis in order to perform data analysis on how to change user behavior. Presently, there are no such devices that perform both of these tasks.

BRIEF SUMMARY OF THE DISCLOSURE

One embodiment of the present invention can be described as a head-mounted device for detecting an alert condition and providing an alert to a user comprising a display unit and a control unit.

The display unit may comprise one or more LEDs and a driver circuit configured to control the brightness of the one or more LEDs. Each LED may be configured to produce a plurality of colors The control unit may comprise a microprocessor in electronic communication with the driver circuit, a memory buffer in electronic communication with the microprocessor, a microphone in electronic communication with the microprocessor, the microphone positioned proximal to an auditory meatus of the user, one or more user input devices in electronic communication with the microprocessor, and a radio transceiver in electronic communication with the microprocessor. The transceiver may be configured to interface with an external computing system. The control unit may be enclosed in a watertight housing. The one or more user input devices may be buttons and the buttons may be positioned on approximately opposite sides of the housing.

The microprocessor may be configured to gather audio samples from the microphone, analyze one or more gathered audio samples for an alert condition, transmit, using the radio transceiver the alert condition, store in the memory buffer the alert condition and when the alert condition occurred, control the driver circuit to change the brightness of the one or more LEDs based on the alert condition, and receive, from the one or more user input devices, a confirmation action from the user. The microprocessor may be further configured to control the driver circuit based on a message received via the radio transceiver.

In one embodiment, the memory buffer may comprise a message queue represented by one or more fixed-width memory structures that represent a status and a transition of each LED. The microprocessor may insert memory structures into the message queue based on the analysis of the one or more gathered audio samples. The microprocessor may retrieve memory structures from the message queue starting from a last index of the message queue and ending at a first index of a message queue.

In another embodiment, the microprocessor may be configured to send and receive messages, each message comprising: a command field, a priority field, a repeat field, one or more LED control fields, an easing field representing a time over which the one or more LEDs should transition from a previous state to a new state, an interpolation field representing whether the new state should ease from off or the previous state, and a duration field representing a time during which the one or more LEDs maintain the new state.

The present invention seeks to provide a solution by providing a indicating device that records and stores data in order to perform analysis. Electronic devices wirelessly paired with the indicating device can activate a light emitting element that indicates information to the user. In one embodiment, the indicating device has an input (such as a button) that enables a user to confirm the indication has been received, thereby dismissing the alert.

In one embodiment, utilizing electronic sensors and network technologies, the present invention indicates risks to the wearer using patterns of light. Additionally, the system stores and aggregates records of exposure levels, alerts, and the user's acknowledgement of their compliance with existing safety protocols. The system may provide a visual representation of this information for users and managers. The present invention provides an instantaneous feedback loop that connects the user, the environment, and the management team.

In another embodiment, workers using the system in environments with hazardous noise levels are notified as those levels change. If a worker approaches an area loud enough to require hearing protection, the worker is prompted with a pattern of light. If the worker is in an environment loud enough where immediate damage can occur, the worker is prompted with a continuous pattern of light until the worker confirms compliance by pressing a button on the device. The amount of time a worker is exposed to each noise level will be aggregated and summed. As a worker approaches a predetermined threshold (for example, OSHA standards for long-term exposure), the management team will be notified allowing them to take actions to mitigate risk.

In another embodiment, during building construction before alarms have been installed, the present invention provides the ability to send notifications to the entire workforce instantly during an emergency.

In another embodiment, workers may be exposed to poisonous gases that can build up or be released unpredictably. By using the present invention, integrated with existing sensor networks, works can be instantly warned to comply with safety protocols (including evacuation) when dangerous gases are detected. The present invention can also be used to alert workers to maintain safe stand-off distances from drilling equipment (i.e., machine guarding).

In another embodiment, the present invention acts like a personal stoplight for industrial lift truck drivers. Sensors measure speed and velocity, and the display warns the driver to slow down if the driver exhibits unsafe behaviors. Shifting loads can be determined by weight transfer on the wheel base. The present invention helps the worker re-align the load before the load tips. When configured with computer vision, proximity sensors, range finding devices, and network technologies, the present invention can alert drivers to slow or stop before a collision.

In another embodiment, the present invention allows warfighters to receive critically important updates to the status of the mission and their surroundings, while maintaining a minimal footprint in their field-of-vision.

In another embodiment, the present invention enables users to receive customized push notifications from their favorite smart phone applications. The present invention can integrate with a software development kit to enable third-party developers to create custom applications for the present invention.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE DISCLOSURE

Figure 1:
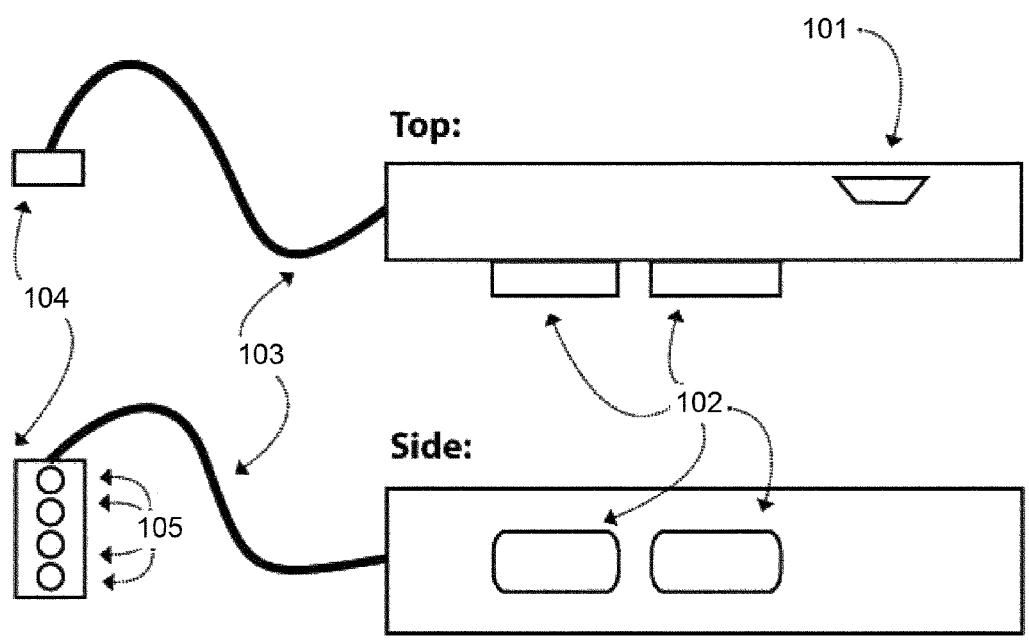
FIG. 1 is a diagram showing a top view and a side of one possible embodiment according to the present invention.

FIG. 1 shows a possible embodiment of a head-mounted display containing USB connector 101, buttons 102, flexible connective cabling 103, LED controller 104, four full color LED array 105. The head-mounted display could also be built in such a way that it is completely enclosed in a watertight seal. The head-mounted display could be remotely programmed over a radio frequency connection with a smartphone, computer, or other computing device. The head-mounted display's battery could be charged using inductive charging.

Figure 2:
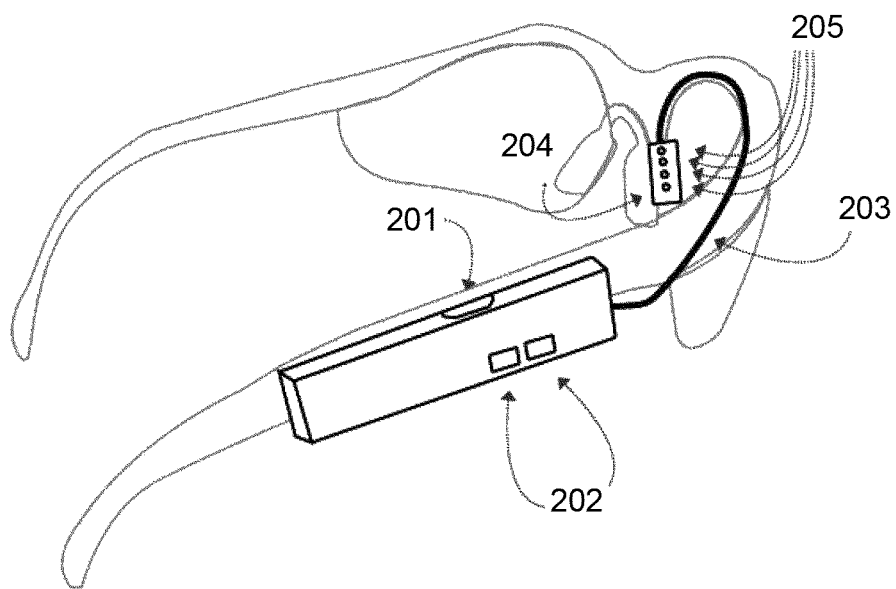
FIG. 2 is a rendering showing one possible embodiment of the present invention configured in situ.

FIG. 2 shows a possible embodiment of a head-mounted display containing USB connector 201, buttons 202, flexible connective cabling 203, LED controller 204, four full color LED array 205 mounted to safety glasses in order to provide real time data for industrial workers or soldiers.

Figure 3:
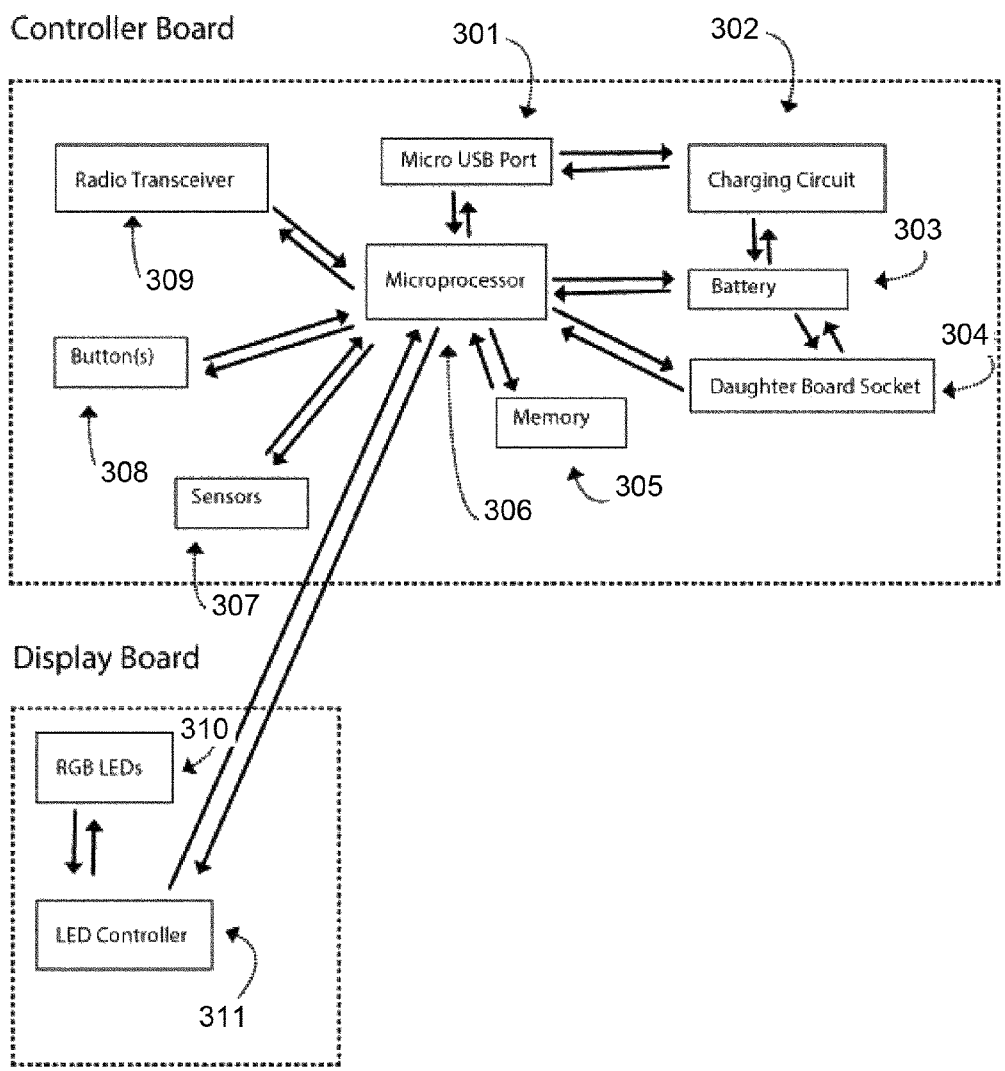
FIG. 3 is a diagram showing communication between the hardware components of one possible embodiment of the present invention.

FIG. 3 shows a block diagram of one a possible embodiment of a head-mounted display system, comprising (i) a display unit, containing one or more lights 310 in one or more colors (the example shown contains four tricolor LEDs) and driver electronics 311 which control the brightness of the light(s) based on control signals received from the control unit, (ii) a control unit, which contains a microprocessor 306, nonvolatile and volatile memory 305, battery 303, battery charging system 302, optional on-board sensors 307, one or more buttons or other user input devices 308, a radio transceiver 309 for wireless communication, an interface for providing power, an interface for providing a data connection to a PC (the example shown uses a microUSB connector 301 to provide both power and data interfaces, and an interface 304 for attaching optional daughter-boards containing additional components or systems, and (iii) a flexible cable connecting the display unit to the control unit, which provides power and control signals to the lights and driver electronics.

Figure 4:
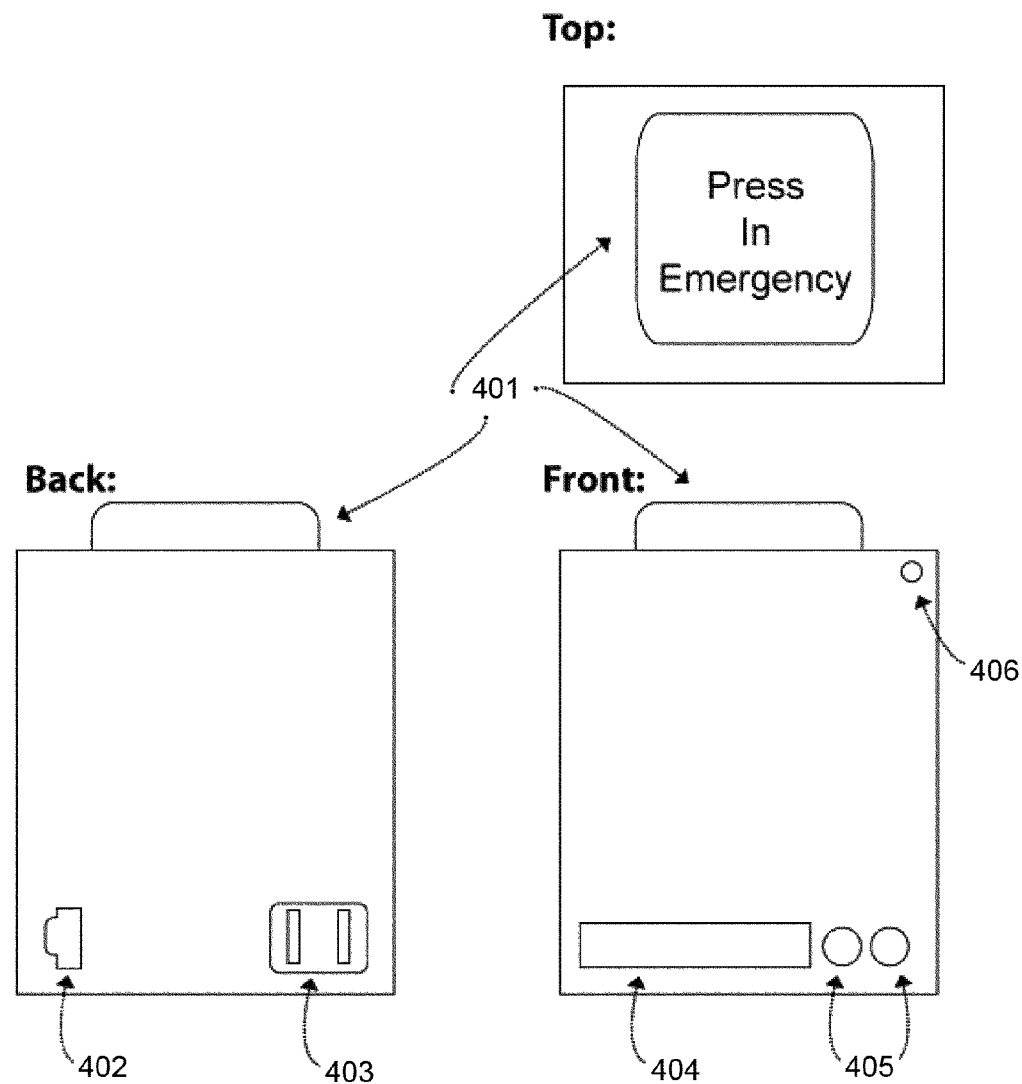
FIG. 4 is a diagram showing an alarm/repeater module according to one embodiment of the present invention.

FIG. 4 shows a possible embodiment of an Emergency Alarm which also acts as a network bridge and wireless repeater ("Mesh Network Device").

The Mesh Network Device can be powered directly by AC current 403 or it can run off an internal battery that is charged using 403.

The Mesh Network Device has a button or switch that can be thrown in case of emergency 401, when this actuator is activated, a site-wide alert is sent to all head-mounted displays (see e.g., FIG. 1) and repeated by all other Mesh Network Devices (see FIG. 4) on the site or in the network. This broadcast is continually repeated until the Mesh Network Devices are reset by an administrator. This functionality can be used to notify all workers on a site of a catastrophic condition (e.g., a fire, chemical spill, gas leak, biological release, radiation hazard).

The Mesh Network Device has a LCD display 404 that is used to display more detailed status information for the devices configuration and connected devices. Different data can be displayed on the LCD display 404 by pressing associated buttons 405 that toggle through a menuing system.

The Mesh Network Device can be connected to a wired network using an 8P8C port 402 or a 8P8C port 402 can be used to create a bridge between an existing sensor technology and the wireless network of head-mounted displays (see e.g., FIG. 1).

The Mesh Network Device automatically form a wireless mesh network with other Mesh Network Device and head-mounted display (see e.g., FIG. 1), allowing companies to create ad hoc safety systems on worksites that do not have the necessary infrastructure or permanence for wired systems.

Figure 5:
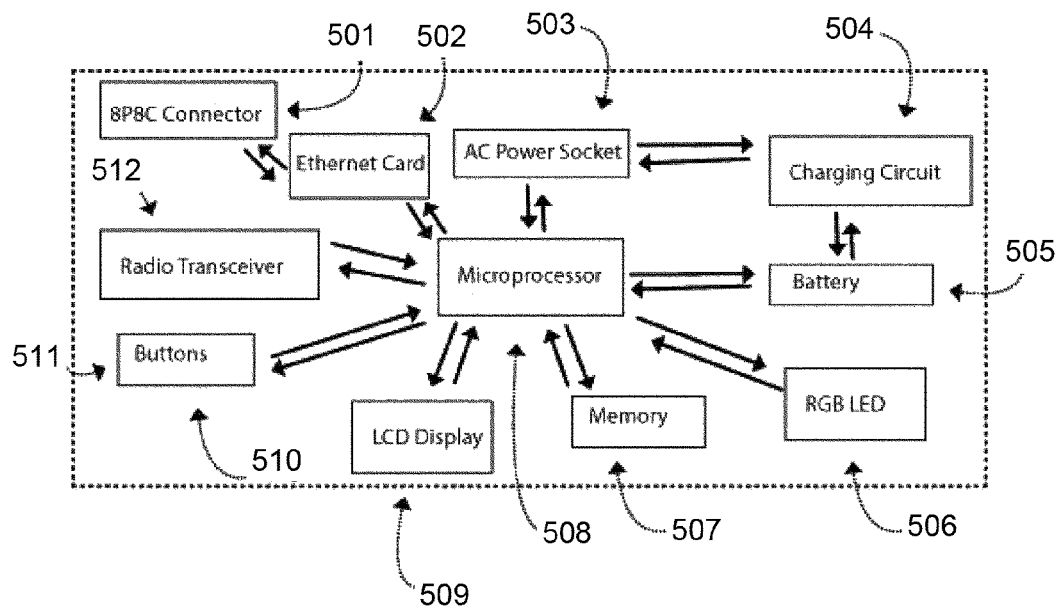
FIG. 5 is a diagram showing communication between the alarm, repeater box, and the hardware components of one possible embodiment of the present invention.

FIG. 5 shows a block diagram of one possible embodiment of an Emergency Alarm which acts as a network bridge and wireless repeater ("Mesh Network Device"). The Mesh Network Device contains an 8P8C connector 501 which allows it to be connected to an existing Ethernet network or optionally to be used as a network bridge and power source for a sensor that uses Power over Ethernet. The Mesh Network Device also contains an Ethernet card 502 that handles necessary network processes. The Ethernet card 502 is connected to the main microprocessor 508.

The microprocessor 508 receives power from either an alternating current power source 503 or a battery 505.

The battery 505 is charged by a charging circuit 504. The charging circuit 504 is powered by an alternating current power source 503.

The Mesh Network Device can indicate its status with an indicator light 506 controlled by the microprocessor 508.

The microprocessor 508 uses volatile and nonvolatile memory 507 to read and write machine readable code and operational data.

The Mesh Network Device can display more detailed status and configuration data through a display 509, the information on this screen can be manipulated by using the associated buttons 511.

The Mesh Network Device can communicate with a wife network, heads up displays, sensors, or other Mesh Network Devices using radio transceivers 512.

Figure 6:
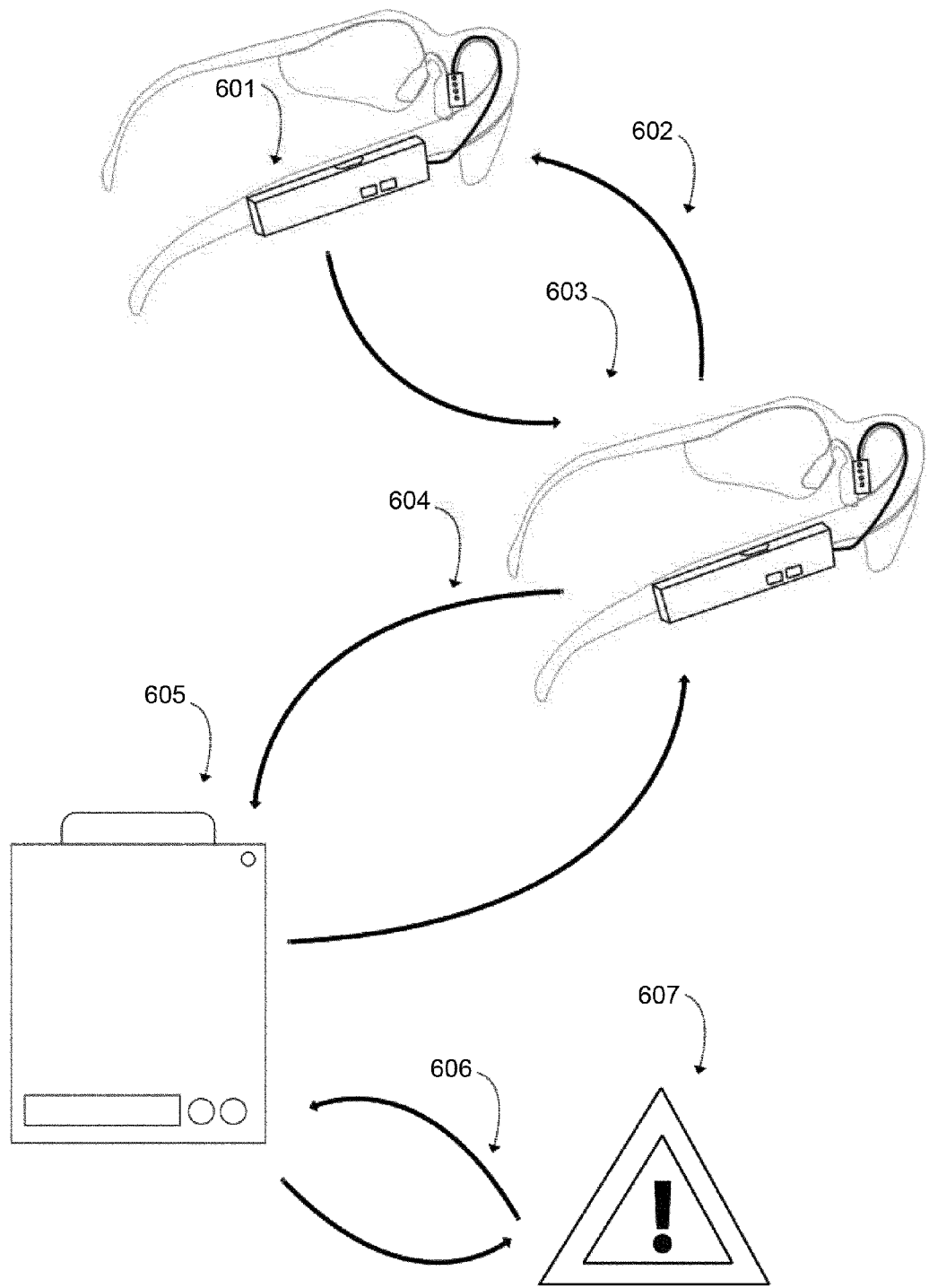
FIG. 6 is a diagram showing one possible implementation of ambient sensor alerting in keeping with the present invention.

FIG. 6 shows an example of head-mounted display 601 communicating wirelessly 602 with another head-mounted display 603 communicating wirelessly 604 to a Mesh Network Device 605 communicating wirelessly 606 to an ambient sensor 607.

The Mesh Network Device 605 communicating with the sensor may interpret sensor data and transmit commands to head-mounted display units 601 & 603 directly 604 or indirectly 602 through intermediary transceivers 603, or it may repeat sensor data without interpretation, to be interpreted by the display units' microcontrollers. Mesh Network Devices and head-mounted display units may use mesh network connectivity status, configured parameters, or other information to determine which display units receive sensor data or commands.

An example of this would be a gas sensor in a mine detecting hazardous levels of a noxious gas in the air. The gas sensor can then send a broadcast message to all workers through the Mesh Network Device providing them instant notification of the event.

Figure 7:
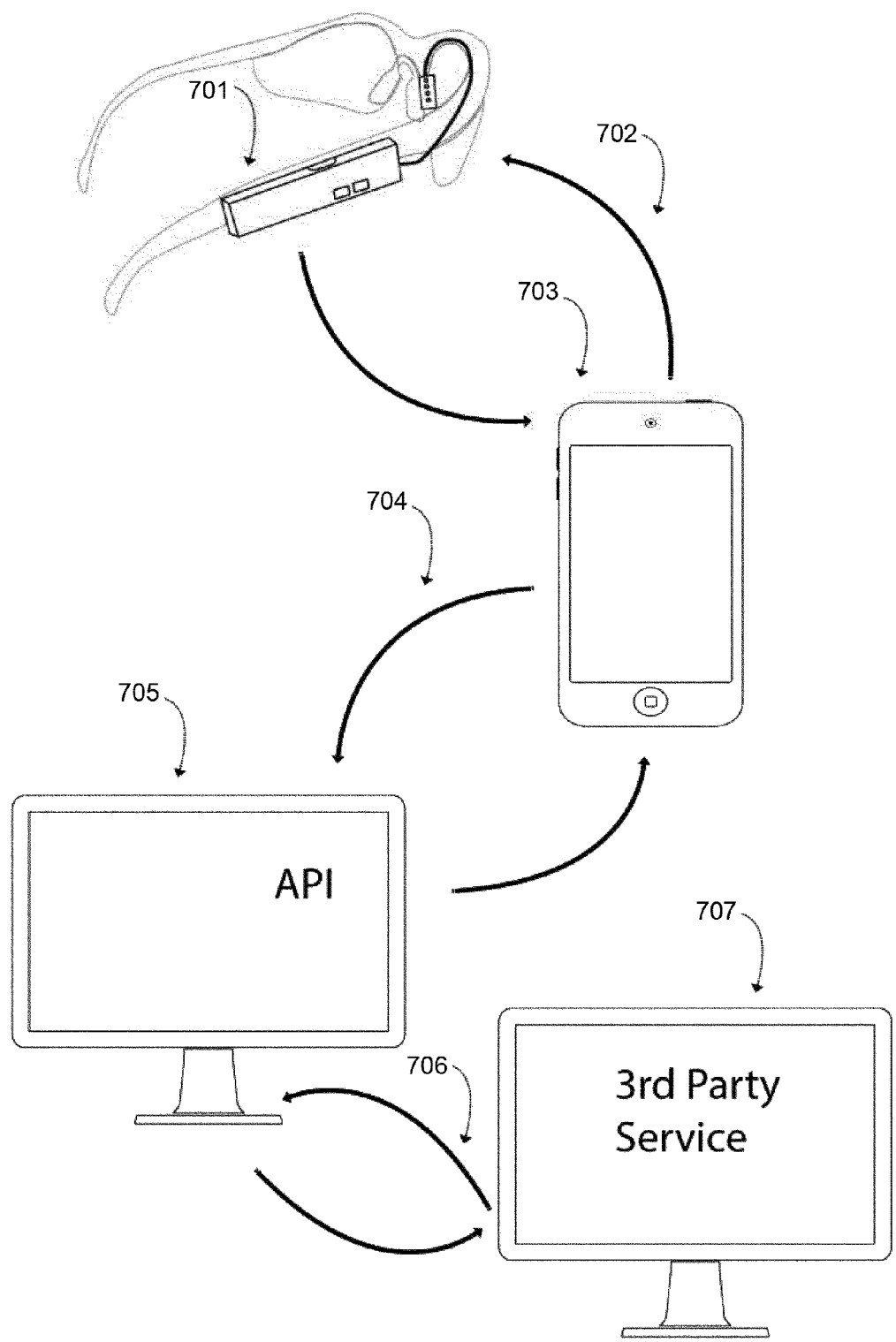
FIG. 7 is a diagram showing one possible implementation of API based communication in keeping with the present invention.

FIG. 7 shows an example of head mounted display 701 communicating wirelessly 702 to an application running on a mobile device 704. The application running on the mobile device 704 can authenticate with a server running an Application Programming Interface (API) 705 and uniquely identifying the user. This authentication allows specific notifications to be sent to the head mounted display 701 and individual data sensed by the head mounted display 701 or the mobile device 703 to be stored remotely by the API server 705. A 3rd party server 707 can send notifications and receive data stored on the API server 705.

An example of this would be a microphone on the head-mounted display measuring ambient noise levels that a worker is exposed to. If the exposure presents a threat to the workers hearing, the head-mounted display can display a pattern of lights reminding the user to wear hearing protection. The recorded sensor data can then be sent over the network to a remote storage location. The data recorded through this system can be analyzed later to mitigate future damages or to provide a defense against fraudulent disability claims.

Figure 8:
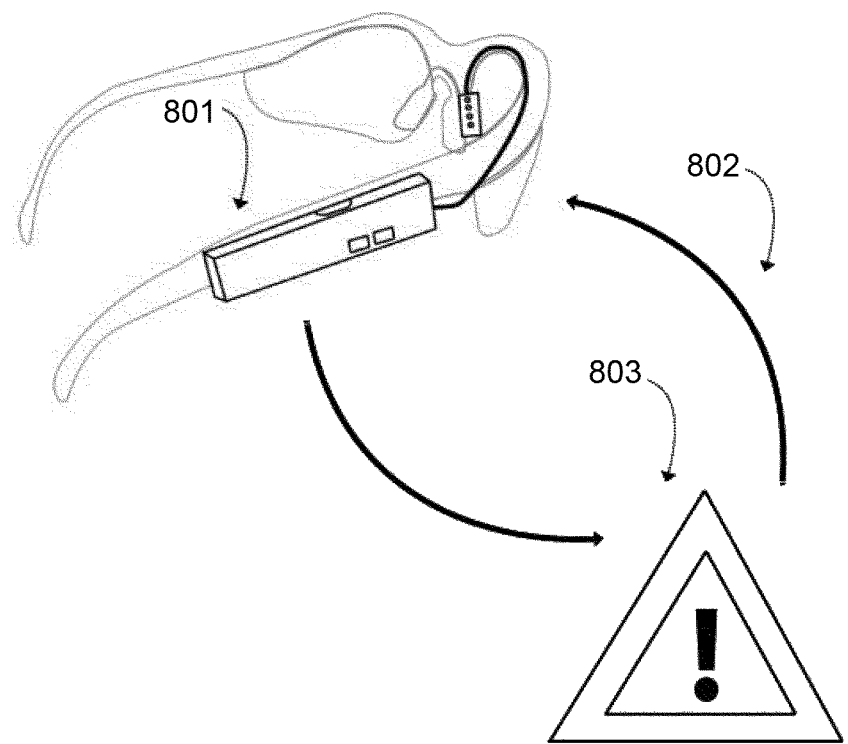
FIG. 8 is a diagram showing one possible implementation of sensor alerting in keeping with the present invention.

FIG. 8 Shows an example of head mounted display 801 communicating wirelessly 802 with an ambient sensor 803. The head mounted display's microprocessor receives sensor information through the wireless transceiver, processes and interprets it, and determines an appropriate pattern to display to the user. Alternately, an implementation could have the sensor 803 process the data being collected and transmit commands to the head-mounted display 801 indicating which light patterns to display.

An example of this would be a non-contact voltage detector in an electrician's glove activating the head-mounted display before the electrician touches a live wire.

Figure 9:
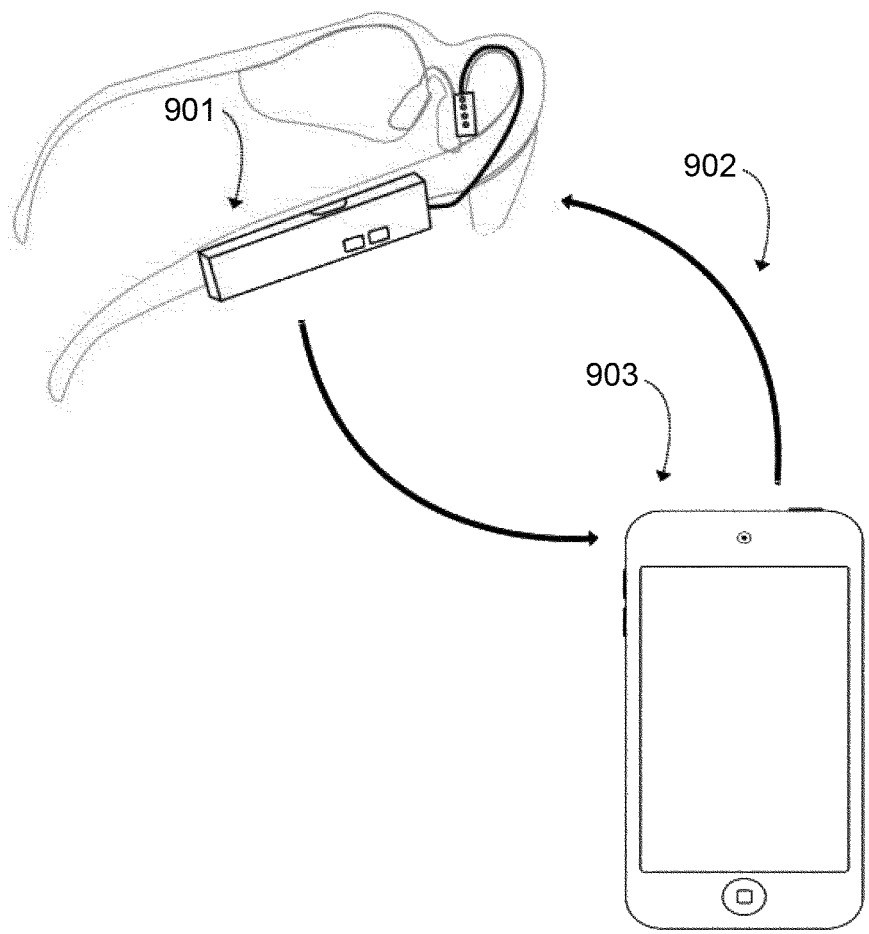
FIG. 9 is a diagram showing one possible implementation of smart device alerting in keeping with the present invention.

FIG. 9 shows an example of head mounted display 901 communicating wirelessly 902 with a mobile application 903 which is receiving data from the sensors on the head mounted display and controlling the lights on the head mounted display based on calculations being performed by machine readable code.

An example of this would be an application on the smart device testing a driver at random intervals for fatigue. Using the display's lights and input devices, the application would prompt the user to identify light patterns as either flickering or steady, thereby allowing the application to measure fatigue-induced variations in the user's flicker fusion threshold. This information could be used to prompt operators to take corrective measures or provide information about fatigue risks.

Figure 10:
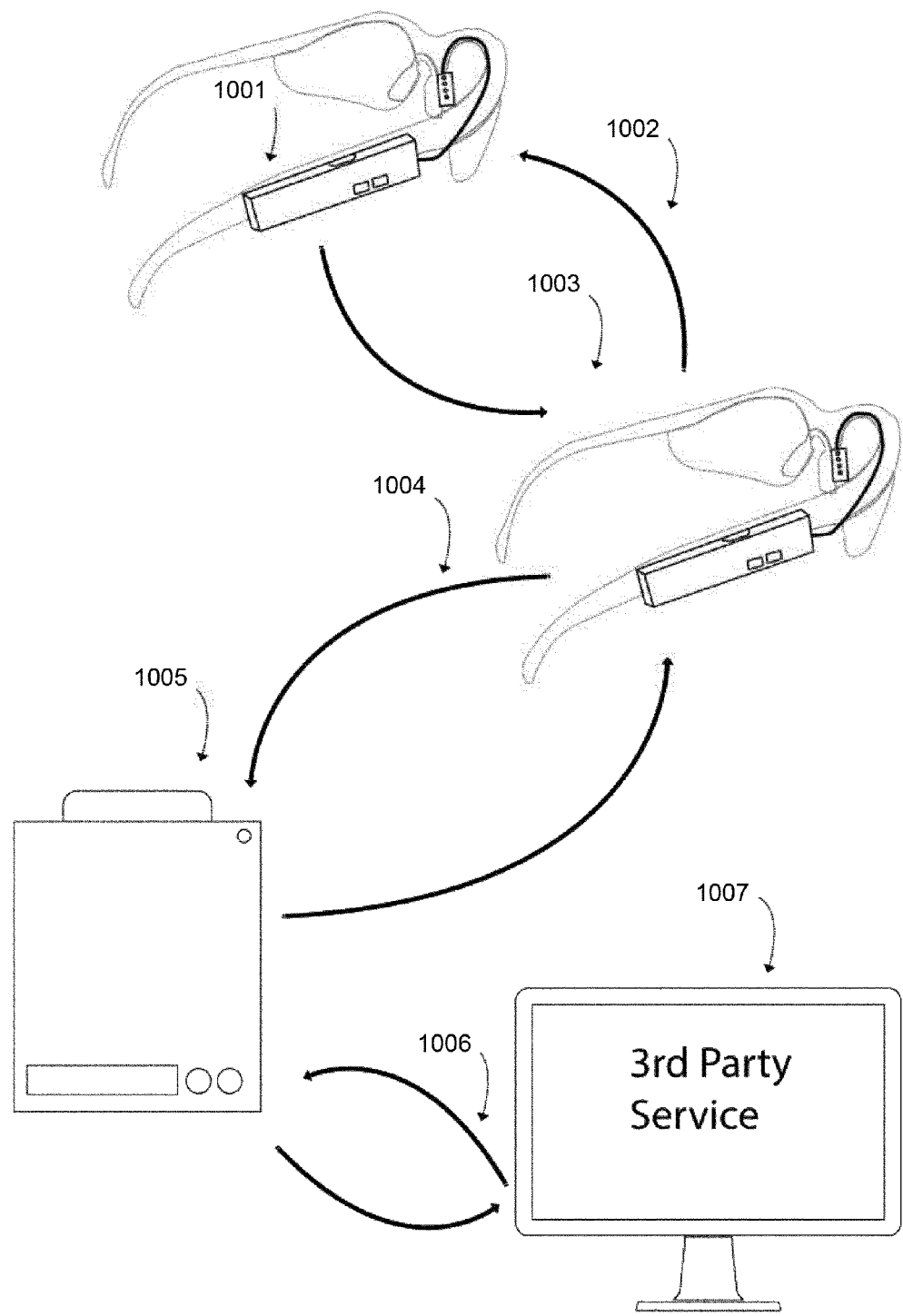
FIG. 10 is a diagram showing one possible implementation of mesh based communication in keeping with the present invention.

FIG. 10 shows an example of head mounted display 1001 communicating wirelessly 1002 with another head mounted display 1003 communicating wirelessly 1004 to an repeater 1005 communicating over a network to 1006 to a 3rd party service or application 1007.

An example of this would be a system in a warehouse determining the location of lift trucks based on the combination of sensor data, computer vision, and other technologies. This system could warn lift truck drivers to slow or stop before a collision occurs around a blind corner.

In one embodiment, the head-mounted display provides a solution for safety and communication issues faced by organizations operating in hazardous work environments. The display enables workers to make data driven decisions while maintaining their situational awareness. The display may consist of four full-color LEDs controlled via sensors over a wireless connection. The display may be configured to be removably mountable to any eye protection device (for example, through use of clamps or clips.

In other embodiment, it may be advantageous for the LEDs to remain off a majority of the time. This may reduce change blindness so that the worker does not become accustomed to the presence of an alarm.

In one embodiment, the LEDs can be instantly activated by network communications and applications running on the workers smartphone. The smartphone can activate the LEDs based on local information such as a change in heart rate, noise, or proximity.

In one embodiment, the head-mounted display utilizes a Bluetooth Low Energy module. This module is supported by most modern smartphone operating systems and many laptops.

Exemplary Embodiments

One embodiment of the present invention is directed toward preventing noise induced hearing loss (NIHL). NIHL is a debilitating disorder that can affect the productivity and quality of life for the afflicted individual. Anthropogenic noise exposure is arguably the chief contributor to the onset of NIHL. With machines found on construction sites and factories capable of producing noise levels scientifically shown to be associated with NIHL, outfitting employees and employers with a dynamic notification and data aggregation system is essential for mitigating the risk of occupationally related NIHL.

In one embodiment, the control unit of the present invention may contain an on-board, relatively flat frequency response (for example, 100-5,000 Hz) microphone, such as a Knowles microphone. The precision and quality of the Knowles microphone across a wide spectrum of frequencies may improve intensity readings across numerous spectral bands commonly found to be generated in industrial environments. The microphone may be placed on the arm of the device which is located near the auditory meatus. Considering that noise level is affected by the amount of distance from a sound source, placing the microphone closer to the wearer's ear may provide a more accurate analysis of the acoustic conditions that the employee is being exposed to than a reading generated from a dosimeter located at a more distant location.

In this embodiment, the display unit is in electronic communication with the microphone and the control unit. Whenever the control unit detects an auditory event that is greater than a pre-determined value, the display unit indicates to the user that they are in a dangerously loud environment. Research has shown that the auditory system has measures in place to adapt to a raise in acoustic intensity, such that a person might not even be aware of the impact of the situation to their auditory health. Having the display unit notify the user when they are in a loud environment will help to ensure the wearer of using proper protective measures. Furthermore, because the threshold can be customized on the device, the device can be configured to use various acoustic standards.

Another major component to this exemplary embodiment is an aggregated data collection network, which is capable of collecting and storing an abundant amount of information about the acoustic conditions of the workplace and each employee. It is well documented that increasing the number of times an individual is exposed to a dangerously loud event, there is an increase in the likelihood of suffering from NIHL. Using the aforementioned Mesh Network, employers are able to record, store, and analyze the number of auditory incidents an employee is exposed to during a specific amount of work time in order to generate a detailed risk analysis for NIHL. Furthermore, the data can be aggregated across numerous employees, across a variety of shifts, and worksite locations to accurately determine which factors (e.g. time of day, work areas, production stage) appear to contribute to NIHL for their workers in order to make appropriate and effective changes to the workplace.

Figure 11:
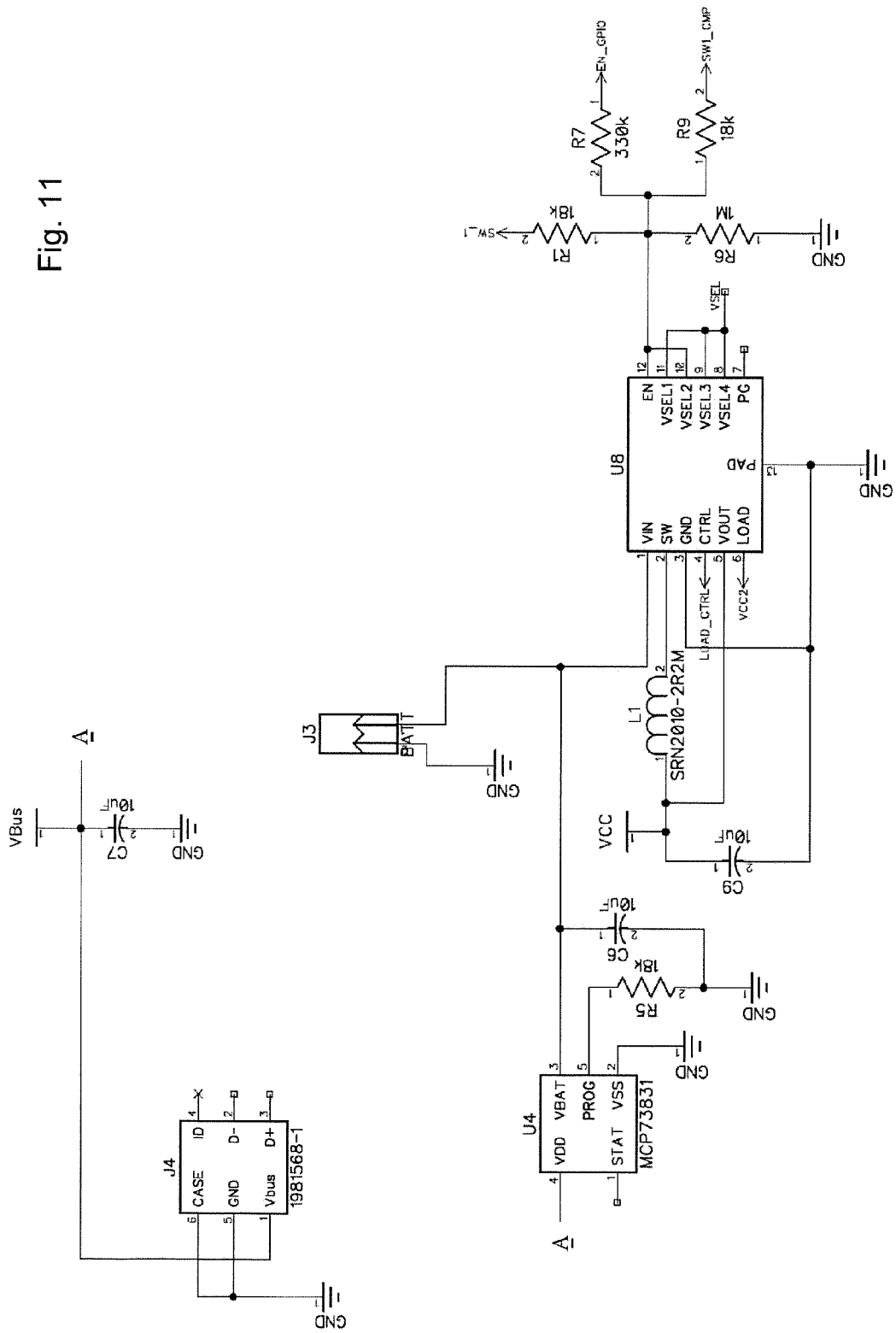
FIG. 11 is a circuit diagram showing one possible implementation of the present invention.
Figure 12:
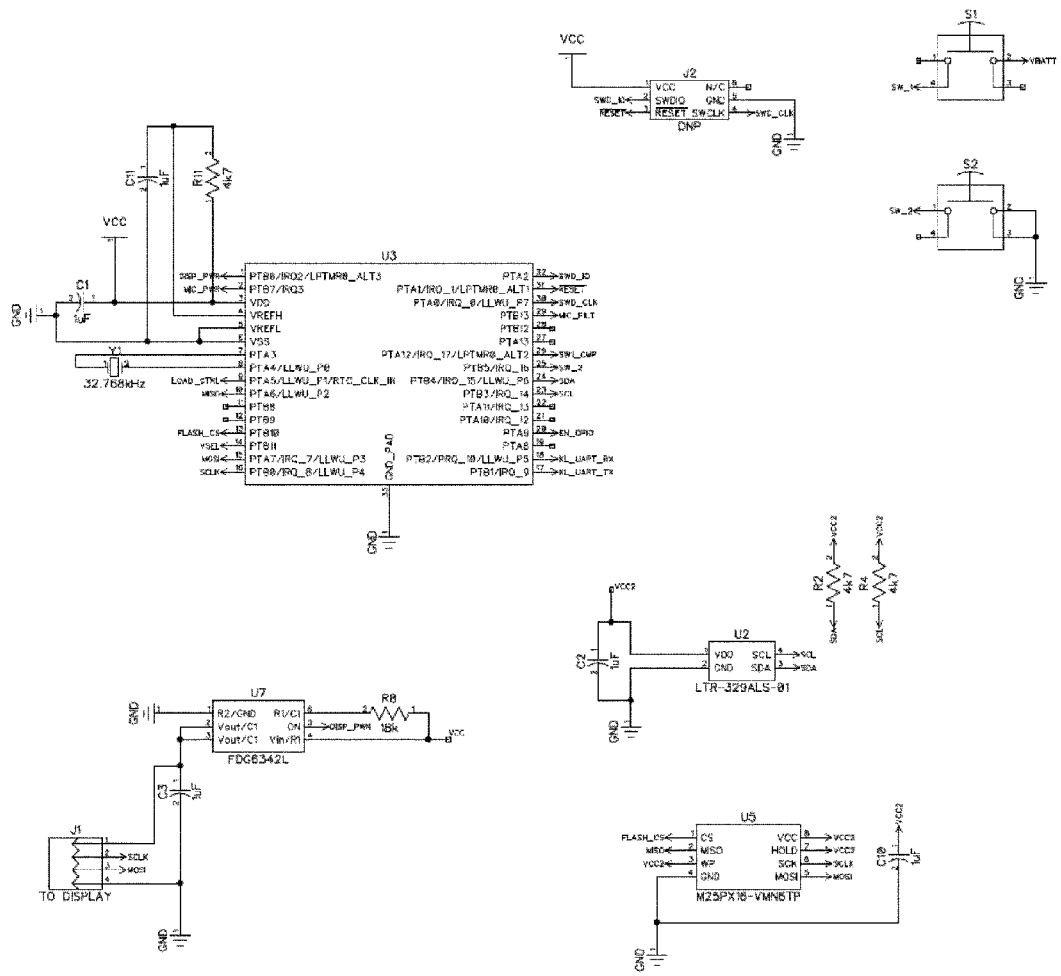
FIG. 12 is a circuit diagram further showing the implementation in FIG. 11.
Figure 13:
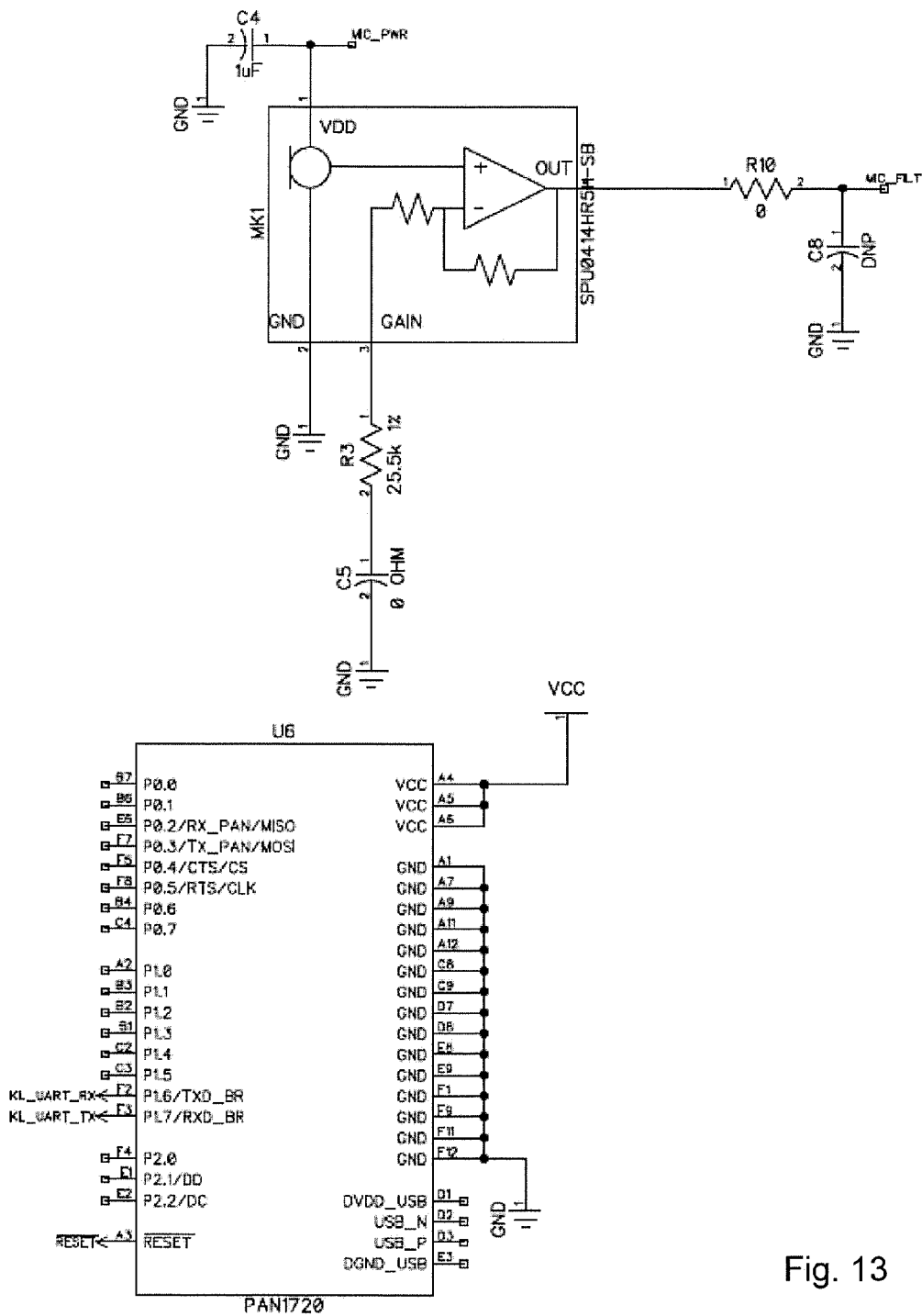
FIG. 13 is a circuit diagram further showing the implementation in FIG. 11.

FIGS. 11-13 are circuit diagrams showing one exemplary hardware implementation of the present invention. In this exemplary embodiment, the device may comprise a battery, a circuit board containing a battery charging circuit, power supply, microcontroller (CPU with memory and integrated analog peripherals), Bluetooth module, flash memory, buttons, microphone, and a stiff, formable cable connecting the main board to a separate circuit board containing an LED driver and four RGB LEDs. The Bluetooth module allows Bluetooth-equipped devices to connect to the CPU to send and receive data including commands and notifications.

The microphone, connected to the microcontroller's analog-to-digital converter through an RC filter, allows the CPU to measure sound pressure levels. The CPU processes sound measurements, data from communication with external devices, and user input, and controls illumination of the LEDs via the LED driver. The power supply converts battery power to a regulated voltage suitable for operating the circuitry, and allows the CPU to control voltage to optimize power consumption during different operating behaviors as well as to deactivate the power supply to eliminate power consumption from the battery. The buttons allow the user to provide input to the CPU, and wake the power supply from a power-off state. The charging circuit controls the transfer of power from the microUSB socket to the battery. Flash memory allows nonvolatile storage of data, including logging of events and alerts.

The microphone input signal may be converted using an a Analog to Digital converter to sample the microphone at a fixed sample rate (typically 32 kHz, 44.1 Khz or 48 kHz). The control unit may gather a group of sample over time and performs a time domain to frequency domain transform to determine the amplitude and power of the signal at fixed frequency intervals. This output may profiled against international standard frequency weighting curves such as IEC 61672 to model the perceived loudness of the signal. If the power levels are above a given threshold for both short term and long term noise exposure, the LED incorporated on the device may be used to alert the wearer so that adequate hearing protection can be used. This status is also communicated wirelessly to a mobile device to monitor the environmental conditions.

In one embodiment, a single button is used both to bootstrap the power supply and as a generic user input. That's accomplished by tying the power supply's ENABLE pin to the button (connected to the battery), a GPIO pin on the microcontroller (powered by the power supply's output), and a comparator input on the microcontroller through large resistances, such that the power supply's ENABLE pin can be activated by a button press or held active by the microcontroller's GPIO pin. The microcontroller can be configured to use its internal comparator and DAC to detect voltage changes from button presses even while the ENABLE line is being held high by the GPIO pin.

One exemplary embodiment of the present invention is a wearable indicator device and system comprising a head-mounted display that monitors ambient noise levels and notifies the user with a visual prompt when certain conditions are met. Such conditions may include a long-term noise exposure at >=85 db or any other noise level that could cause noise induced hearing loss (NIHL) or a noise level that can cause immediate NIHL (e.g., >100 db). In situations where long-term noise exposures may cause hearing loss, the head-mounted display may prompt user once, at which time the head-mounted display may not prompt the user again unless the ambient noise exceeds 100 db, 15 minutes have elapsed, or the noise level has dropped to <65 db for more than five minutes. The prompt pattern should be based on creating a moderate response from the user—it is informational and should be short enough to not overly distract the user.

In situations that may cause immediate NIHL, the prompt may continue until dismissed by the user. If dismissed, the head-mounted display should not prompt again unless 30 minutes have elapsed or the noise level has dropped to <65 db for more than five minutes.

In one exemplary embodiment, the wearable indicator device may be configured to negotiate with a Bluetooth Low Energy (BLE) device and implement a proprietary messaging protocol. The head-mounted display may display a pre-determined pattern to indicate successful pairing. If no pairing is present, the head-mounted display may blink a different predetermined pattern until dismissed by the user or a connection is established. The wearable indicator device may transmit readings over BLE using the proprietary messaging protocol. If no BLE communication is available, the device may store data in a local buffer. In one embodiment, the following data may be stored or transmitted: (1) noise amplitude and associated time stamp, (2) button press and associated time stamp, (3) display acknowledgements and associated time stamp; and (4) errors and associated time stamp.

dashboard application may make http requests to the cloud server through our RESTful API. The cloud server retrieves the pertinent data from the database, runs algorithms on the data to prepare it to be transferred, and then responds to the http request, sending the preprocessed data to the dashboard. The dashboard then applies other algorithms to the data it has received to prepare it for visualization. The dashboard may take further inputs from the user and apply transformations to the locally cached data and visualizations, or it may request more data from the cloud server. The dashboard also has capabilities to prompt the HUD of individual users or work groups through direct user interaction or scheduled events. The dashboard user can press an on screen button that will trigger a series of lights to be turned on in the targeted workers HUD. This prompt is transmitted by the dashboard making an http request to the cloud server, the cloud server then stores the request in the database for later review, it also runs algorithms on the request to determine the addressed user by making requests to the database server. Once the appropriate user(s) have been determined, the cloud server may contact a 3rd party provider to send a "push notification" to the addressed users mobile device.

Packets may be formed as follows:

Packet Definition

| MSG/CMD | PRI/ARG | REP | L0 | L1 | L2 | L3 | EASING | INTERPOLATION | DURATION |
|---|---|---|---|---|---|---|---|---|---|
| BOOL | BOOL | INT | INT | INT | INT | INT | INT | BOOL | INT |
| 1 BIT | 1 Bit | 1 Byte | 3 Byte | 3 Byte | 3 Byte | 3 Byte | 3 Bytes | 1 Bit | 3 Bytes |
| CHR | INT | NULL | NULL | NULL | NULL | NULL | NULL | NULL | NULL |
| 3 Bytes | 1 Byte | | | | | | | | |

Related to the proprietary messaging protocol, the device may have a message queue stored in local memory. The message queue may be represented by a fixed width memory structure of predefined characteristics that will control the display and transition of LED states according to programmed rules. Each complete memory structure will be referred to as a packet. Each packet represents a distinct light state for the hardware, and instructions on how to transition to the state from the previous state. Malformed packets may be ignored.

The messaging protocol may allow for workers to be assigned different devices on different days, but the data collected is stored in a format that allows the system to identify which worker had the device on at what time. Therefore, the system is capable of analyzing and visualizing exposure data, prompts, and acknowledgements on a per worker basis throughout the history of usage.

The system may be designed to be sensor-agnostic. The controller system may handle communication from sensors outside the architecture then sort and assign them in the correct order to the correct devices. This creates the possibility of a network of sensors that can drive data to groups of HUDs in contrast to current point-to-point systems, e.g. a Smoke sensor tied directly or directly via purpose built intermediary devices to an alarm klaxon.

The proprietary protocol may transmit information to a cloud-based server by making http requests to a RESTful API in JSON format. The cloud server that handles the requests sent from the computing device then takes the data and stores it in a database for later retrieval.

Figure 14:
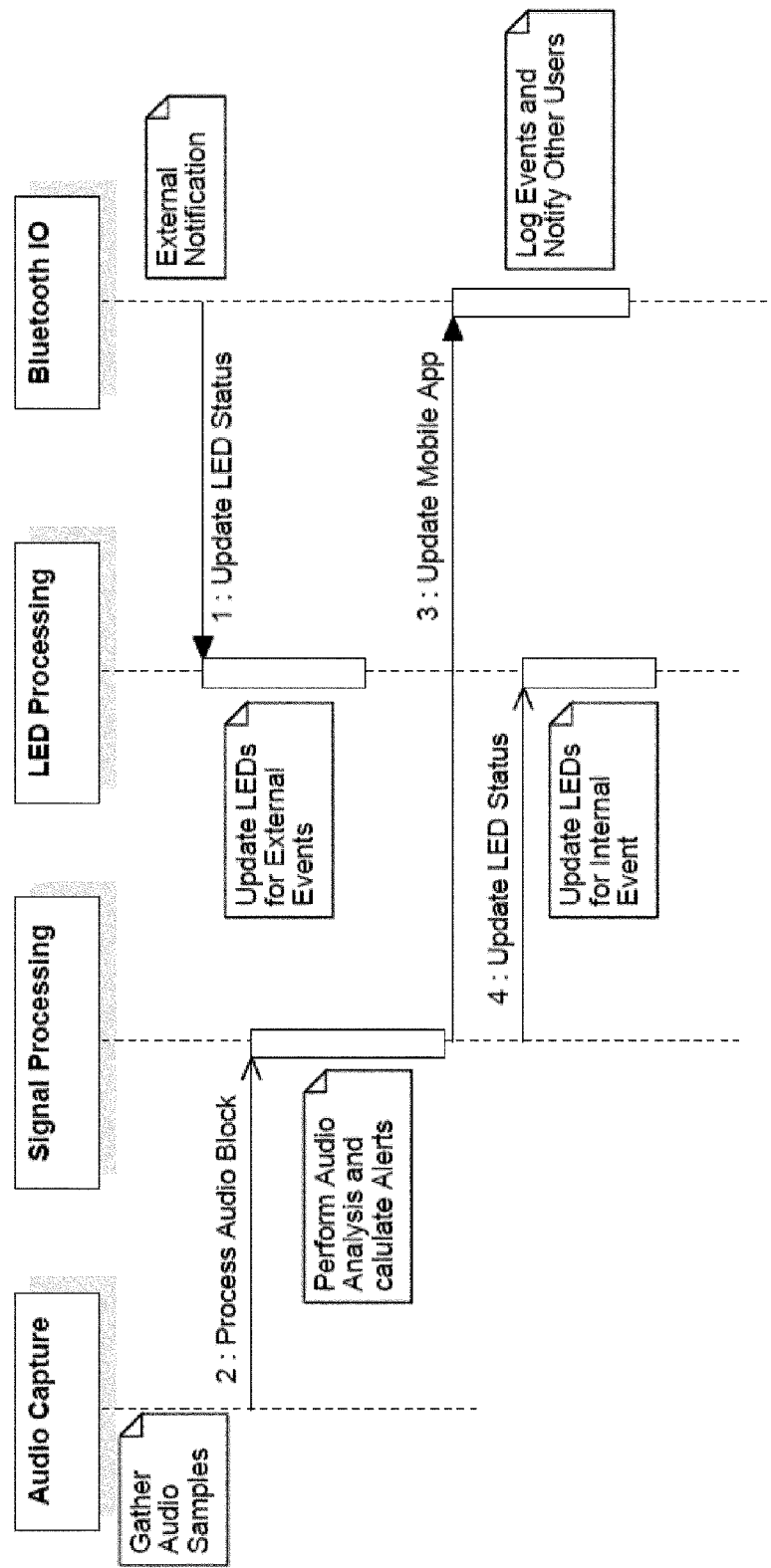
FIG. 14 is a sequence diagram showing the flow of information in one possible implementation of the present invention.

FIG. 14 is a sequence diagram showing the flow of information in one possible implementation of the present invention. For analyzation and visualization, an analytics The MSG/CMD field may be a dual-purpose field. For example, if the input is integer, it will consider all messages with the same integer to be a part of the same message group. A message group is an ordered group of packets that are managed in the message queue as one group. Operations that add or remove messages remove groups of signals. A message may contain between 1 and N signals. Unless otherwise specified, commands are processed in order and wait for a moment of opportunity. Some commands once received will always "line jump" and take immediate effect. Possible commands are listed below:

| CMD | ARG | Description |
|---|---|---|
| POP | INT | Remove INT messages from the end of the message queue (last index). Default 1 |
| SFT | INT | Remove INT message from the start of the message queue (first index). Default 1 |
| CLR | NULL | IMMEDIATELY removes the currently executing message group and sets all lamps to off, then proceeds with next message in queue. Signals received while the clear is occurring will be processed normally. |
| XXX | NULL | IMMEDIATELY removes currently executing message groups and all subsequent messages, sets all lamps to off, then awaits further instructions. Instructions received while the purge is occurring will be discarded. |
| OFF | NULL | Turns off the device |
| DIE | NULL | IMMEDIATELY turns off the device |
| TST | INT | Perform LED or SYSTEM test defined by the INT, developer's discretion |
| STP | NULL | Stop the currently repeating message group. Effectively sets the REP count to 1 for the message group so that it will finish its current iteration and then proceed with the rest of the message queue in memory |

-continued

| CMD | ARG | Description |
|---|---|---|
| CNT | NULL | Blink L0 a number of times equal to the number of messages in the message queue.<br>Blink L1 a number of times equal to the number of signals in the message queue. |

The PRI/ARG field may be a dual-purpose field. If the most significant bit is an integer this will be reckoned as a bit. 0 means that the message and all of the signals in this message, are added to the end of the message queue in memory. 1 means the message is "priority" and will be added (unshift) to the front of the message queue in memory such that the first signal of this message group will be at index 0. While PRI is attached as a bit to each signal in the message, and should be the same for each signal in the message, only the first instance of PRI in a message group is obeyed. If the most significant bit is a character, this will be reckoned as a int and be used as an argument for the command identified by the CMD field.

The REP field is a 1 Byte Integer representing the number of time the message group should be repeated. Each signal in the message group will be executed once, including easing, interpolation, and duration in order from first to last for the number of times indicated by REP. At the beginning of each REP is a moment of opportunity for a command or new high priority message to be processed. REP value of 0 shall indicate infinite repetition that will only be stopped by a subsequent command.

L0, L1, L2, L3 are fields representing the RGB setting for the specified LED.

The EASING field is a 3 Byte integer representing the number of milliseconds over which the LED should transition from previous state to the new signal. Easing may use a flat, linear curve from previous to new signal. Easing between certain values, such as complimentary colors may create unusual or unpleasant effects in human vision. It is up to the application developer to avoid visual aberrations when using easing. Easing duration may be in addition to the duration value. An Easing of 0 describes an immediate jump from previous state to new state. Durations that are not evenly divisible by the clock speed of the hardware shall have the nonzero remainders ignored.

The INTERPOLATION field is a 1 Bit field representing whether the new signal should ease from off (000000) or from the previous signal state. This is intended to facilitate many blinking and pulsing behaviors without needing to specifically define "off" signals for each LED.

The DURATION field is a 3 Bytes field representing the number of milliseconds the four LEDS should maintain this state following any easing duration. Duration of 0 means that the signal will remain in the specified state until interrupted. It is not recommended to use this except in limited cases. Durations that are not evenly divisible by the clock speed of the hardware shall have the nonzero remainders ignored.

Message Packet Example (Hex Representation)

| MSG | PRI | REP | L0 | L1 | L2 | L3 | EASING | INTERPOLATION | DURATION |
|---|---|---|---|---|---|---|---|---|---|
| 100001 | 0 | 1 | 000000 | FFFFFF | AA0000 | 00AA00 | 000092 | 1 | 00003C |

Command Packet Example (Ascii Representation)

| CMD | ARG |
|---|---|
| POP | 1 |

MSG Packet

| Byte | Data Type | Name | Description |
|---|---|---|---|
| 0 | Bit 7<br>Bit 6<br>Bit 5<br>Bits 4:0 | Flags | MSG/CMD Flag - 1 denotes MSG<br>Priority Msg<br>Interpolate<br>Group ID (0-31) |
| 1 | Byte | Repetitions | Only the first member of the group needs to specify this. |
| 2 | Byte | LED 0 Red | Allows a brightness range of 0-255 |
| 3 | Byte | LED 0 Green | |
| 4 | Byte | LED 0 Blue | |
| 5 | Byte | LED 1 Red | |
| 6 | Byte | LED 1 Green | |
| 7 | Byte | LED 1 Blue | |
| 8 | Byte | LED 2 Red | |
| 9 | Byte | LED 2 Green | |
| 0 | Byte | LED 2 Blue | |
| 11 | Byte | LED 3 Red | |
| 12 | Byte | LED 3 Green | |
| 13 | Byte | LED 3 Blue | |
| 14<br>15 | Word | Easing | In units of 1/100 sec - allows max of 655.35 seconds |
| 16<br>17 | Word | Duration | In units of 1/100 sec - allows max of 655.35 seconds |

CMD Packet

| Byte | Data Type | Name | Description |
|---|---|---|---|
| 0 | Bit 7<br>Bits 6:0 | Flags | MSG/CMD Flag - 0 denotes CMD Command |
| 1 | Byte | Argument | |

Values for Command

| | | |
|---|---|---|
| CMD_POP | 0x00 | remove <arg> messages from the end of the queue |
| CMD_DEL | 0x01 | remove <arg> messages from the start of the queue |
| CMD_CLR | 0x02 | remove the currently executing message from the queue |
| CMD_XXX | 0x03 | remove all messages from the queue and set the lamps to off |
| CMD_OFF | 0x04 | Turn the device off |
| CMD_DIE | 0x05 | Immediately turn the device off |
| CMD_TST | 0x06 | Perform self-test specified by <arg> |
| CMD_STP | 0x07 | Stop the current message group |
| CMD_CNT | 0x08 | Blink LED0 indicating the # of messages in the message queue |

In another exemplary embodiment, the device may receive properly formed messages sent over a BLE connection and render them on the display. If more than one message is received, the messages may be queued or repeated alternately until requirements specified in the message are met or the display has been dismissed by a button press on the control unit.

In one exemplary embodiment, the control unit has two buttons placed on approximately opposite sides of the control unit housing. When both buttons are depressed simultaneously during run-time, the device may be reset. When both buttons are depressed simultaneously during initialization, the device may enter a calibration mode. When the top button (meaning the top button when the device is worn) is depressed and held during run time, the device may forget the current BLE pairing and listen for a new BLE connection. When the top button is depressed end held while the device is off, this action will act as a signal to power the device.

In one embodiment, the system will further comprise a driver, such as a library (for example in NodeJS) that will provide a human-readable and easily manipulated object interface for sending messages to the device. The library may be paired with an Open Source BlueTooth library to handle the mechanics of BlueTooth 4 Low Power communication. On top of the BlueTooth library the driver will allow for a device to be paired, addressed, messaged, and controlled from a desktop and a mobile platform. The driver may allow for one or more devices to be connected to one or more controllers for the purpose of bi-directional communication. The driver may follow normal NPM library patterns to be included and instantiated. The driver may have several methods to message and control the head-mounted device. The device may keep an internal queue of messages represent by groups of signals over which it will operate or iterate. The methods may control connecting to the glasses, dealing with the statefulness by wrapping the BlueTooth library for consistency, and manipulating the message queue on the glasses.

The driver may instruct the glasses to remove depth elements starting from the last index of the message queue counting backwards. The removal may happen at the next moment of opportunity after the current message has finished processing or begins a new loop. The default depth may be 1 element. The driver may send a message to the device with the most significant bit set to "POP" followed by a one byte integer representing the number of messages (not signals) to be removed.

The driver may instruct the glasses to remove depth elements starting from the 0th index of the message queue counting upwards. The removal may happen at the next moment of opportunity after the current message has finished processing or begins a new loop. The default depth may be 1 element. The driver may send a message to the device with the most significant bit set to "SFT" followed by a one byte integer representing the number of messages (not signals) to be removed.

The driver may instruct the device to insert the message to the new the 0th element of the message queue. The addition may happen at the new moment of opportunity after the current message has finished processing or beings a new loop. The message is required or the method will return an error. The driver may send the message specified with the priority bit set to 1.

Although the present invention has been described with respect to one or more particular embodiments, it will be understood that other embodiments of the present invention may be made without departing from the spirit and scope of the present invention.

Hence, the present invention is deemed limited only by the appended claims and the reasonable interpretation thereof.

What is claimed is:

1. A head-mounted device for detecting an alert condition and providing an alert to a user comprising:
 a display unit having:
  one or more light emitting diodes (LEDs);
  a driver circuit configured to control the brightness of the one or more LEDs; and
 a control unit having:
  a microprocessor in electronic communication with the driver circuit;
  a memory buffer in electronic communication with the microprocessor;
  a microphone in electronic communication with the microprocessor, the microphone positioned proximal to an auditory meatus of the user;
  one or more user input devices in electronic communication with the microprocessor; and
  a radio transceiver in electronic communication with the microprocessor, the transceiver configured to interface with an external computing system;
 wherein the microprocessor is configured to:
  gather audio samples from the microphone;
  analyze one or more gathered audio samples for an alert condition;
  transmit, using the radio transceiver the alert condition;
  store in the memory buffer the alert condition and when the alert condition occurred;
  control the driver circuit to change the brightness of the one or more LEDs based on the alert condition;
  receive, from the one or more user input devices, a confirmation action from the user; and
 wherein the driver circuit is controlled by sending and receive messages, each message comprising:
  a command field;
  a priority field;
  a repeat field;
  one or more LED control fields;
  an easing field representing a time over which the one or more LEDs should transition from a previous state to a new state;
  an interpolation field representing whether the new state should ease from off or the previous state; and
  a duration field representing a time during which the one or more LEDs maintain the new state.

2. The device of claim 1, wherein each LED is configured to produce a plurality of colors.

3. The device of claim 1, wherein the control unit is enclosed in a watertight housing.

4. The device of claim 1, wherein the microprocessor is further configured to control the driver circuit based on a message received via the radio transceiver.

5. The device of claim 1, wherein the memory buffer comprises a message queue represented by one or more fixed-width memory structures that represent a status and a transition of each LED.

6. The device of claim 5, wherein the microprocessor retrieves memory structures from the message queue starting from a last index of the message queue and ending at a first index of a message queue.

7. The device of claim 5, wherein the microprocessor inserts memory structures into the message queue based on the analysis of the one or more gathered audio samples.

8. The device of claim 1, wherein the one or more user input devices are buttons.

9. The device of claim 8, wherein the control unit is enclosed in a housing, and the buttons are positioned on approximately opposite sides of the housing.

\* \* \* \* \*